US011635428B2

United States Patent
Miki et al.

(10) Patent No.: US 11,635,428 B2
(45) Date of Patent: Apr. 25, 2023

(54) MOLECULE DETECTING DEVICE AND MOLECULE DETECTING METHOD

(71) Applicant: KABUSHIKI KAISHA TOSHIBA, Tokyo (JP)

(72) Inventors: Hiroko Miki, Kawasaki Kanagawa (JP); Atsunobu Isobayashi, Yokohama Kanagawa (JP); Yoshiaki Sugizaki, Fujisawa Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 49 days.

(21) Appl. No.: 17/017,113

(22) Filed: Sep. 10, 2020

(65) Prior Publication Data
US 2021/0293802 A1 Sep. 23, 2021

(30) Foreign Application Priority Data
Mar. 17, 2020 (JP) .............................. JP2020-046761

(51) Int. Cl.
*G01N 33/543* (2006.01)
*G01N 33/53* (2006.01)
*G01N 27/414* (2006.01)

(52) U.S. Cl.
CPC ... *G01N 33/54373* (2013.01); *G01N 27/4145* (2013.01); *G01N 33/5308* (2013.01)

(58) Field of Classification Search
CPC .... B01L 3/502; B01L 3/00; B01L 3/50; B01L 3/5027; B01L 3/502715; G01N 33/54373;
(Continued)

(56) References Cited

U.S. PATENT DOCUMENTS

2006/0205061 A1* 9/2006 Roukes ................. B01L 3/5027
435/287.2
2013/0244337 A1* 9/2013 Meinhart ............. G01N 21/658
29/17.2
(Continued)

FOREIGN PATENT DOCUMENTS

JP  2016-85737 A  5/2016
JP  2016186426 A * 10/2016
(Continued)

OTHER PUBLICATIONS

Cabane et al., "Stimulus-Responsive Polymers and Their Applications in Nanomedicine", Biointerphases (2012) 7:9, 28 pages (Year: 2012).*
(Continued)

*Primary Examiner* — Ellen J Marcsisin
*Assistant Examiner* — Jennifer H. Tieu
(74) *Attorney, Agent, or Firm* — Finnegan, Henderson, Farabow, Garrett & Dunner, LLP

(57) ABSTRACT

According to one embodiment, a molecule detecting device includes a capturing section, a releasing section, and a detecting section. The capturing section is configured to, by combining a target molecule and a solubilizing agent with each other and thereby creating a composite body, capture the target molecule in a carrier liquid. The releasing section is configured to make the composite body release the target molecule therefrom in the carrier liquid. The detecting section is configured to carry out detection of the target molecule in the carrier liquid.

7 Claims, 8 Drawing Sheets

(58) Field of Classification Search
CPC ........... G01N 27/4145; G01N 33/5308; G01N 33/00; G01N 27/414
See application file for complete search history.

(56) References Cited

U.S. PATENT DOCUMENTS

| | | |
|---|---|---|
| 2016/0117584 A1 | 4/2016 | Yoneda et al. |
| 2016/0329368 A1 | 11/2016 | Ohmura |
| 2017/0350854 A1 | 12/2017 | Yamada et al. |
| 2017/0350882 A1* | 12/2017 | Lin ................. G01N 33/54353 |
| 2018/0272340 A1* | 9/2018 | Govyadinov ....... B01L 3/50273 |
| 2018/0275084 A1 | 9/2018 | Saito et al. |
| 2020/0080977 A1 | 3/2020 | Isobayashi et al. |

FOREIGN PATENT DOCUMENTS

| | | |
|---|---|---|
| JP | 2016-213823 A | 12/2016 |
| JP | WO2017/025996 A1 | 2/2017 |
| JP | 2018-72745 A | 5/2018 |
| JP | 2018-163146 A | 10/2018 |

OTHER PUBLICATIONS

Yuko Ishida et al., "Discovery of a New Protein that Carries an Ant Signal Transmitter—Niemann-Pick C2 Type Protein Localized in Antennal Sensilla of Black Ant Worker," Kagaku to Seibutsu, vol. 53, No. 2, pp. 66-68 (2015).

Gong-Yan Liu et al., "Near-infrared light-sensitive micelles for enhanced intracellular drug delivery," Journal of Materials Chemistry (22), pp. 16865-16871 (2012).

Masamichi Nakayama, "Thermoresponsive polymeric materials for drug delivery systems," Drug Delivery System (23-6), pp. 627-636 (2008).

* cited by examiner

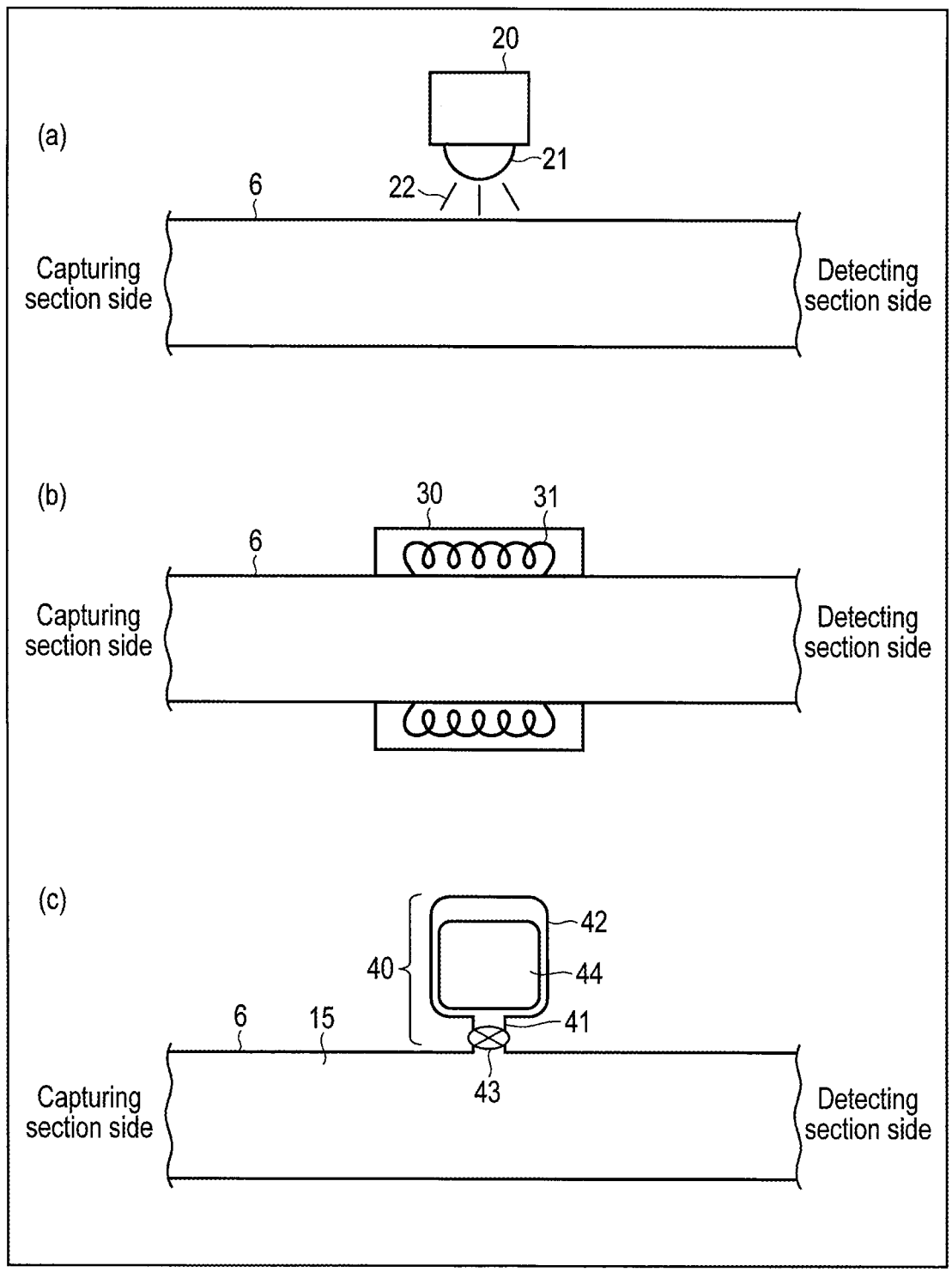
F I G. 2

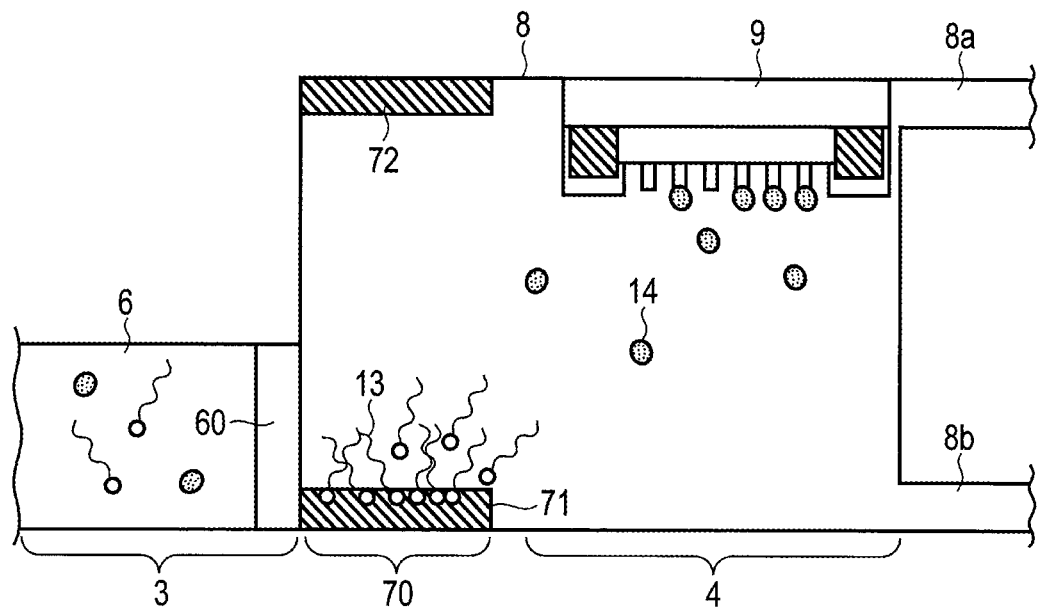
F I G. 9
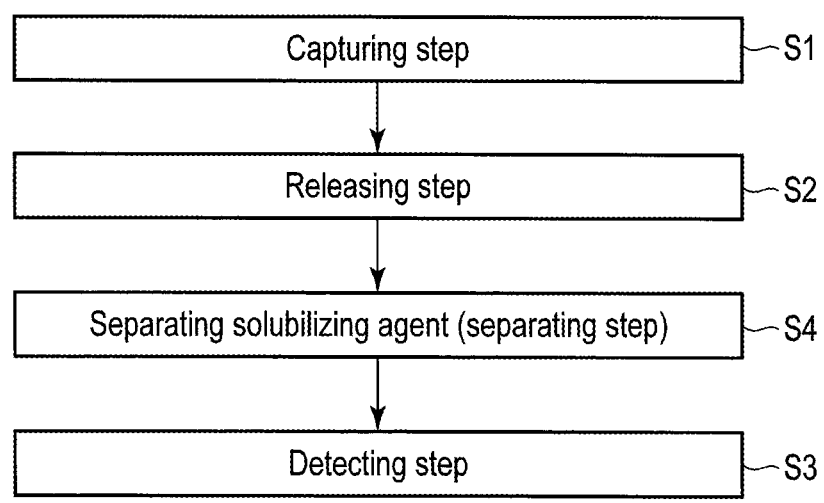
F I G. 10

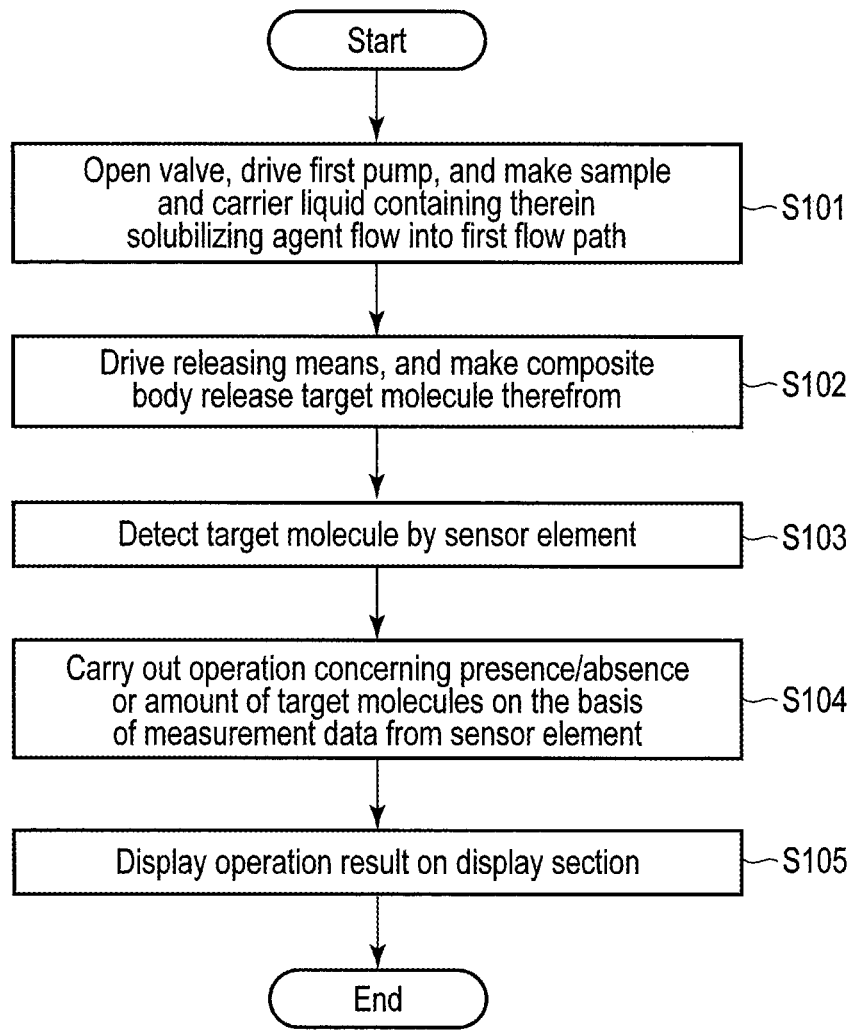
F I G. 12

MOLECULE DETECTING DEVICE AND MOLECULE DETECTING METHOD

CROSS-REFERENCE TO RELATED APPLICATIONS

This application is based upon and claims the benefit of priority from Japanese Patent Application No. 2020-046761, filed Mar. 17, 2020, the entire contents of which are incorporated herein by reference.

FIELD

Embodiments described herein relate generally to a molecule detecting device and molecule detecting method.

BACKGROUND

In recent years, regarding substance detection in the air, baggage inspection in an airport, diagnosis of illness, and the like, use of a sensor configured to detect odor molecules attracts a growing interest. Under these circumstances, a high degree of enhancement in sensitivity and high degree of improvement in accuracy of the odor detecting sensor are required.

As the odor detecting sensor, there is a sensor contrived in such a manner as to detect odor molecules after once dissolved in advance in a liquid. The odor molecules are hydrophobic in many cases, and hence it is required that the odor molecules be dissolved in the liquid as much as possible before detection.

BRIEF DESCRIPTION OF THE DRAWINGS

FIG. 2 shows enlarged cross-sectional views each of which is an enlarged cross-sectional view showing an example of a releasing section of the first embodiment.

FIG. 9 is an enlarged view showing an example of a situation of a detecting section of a second embodiment in the usage state.

FIG. 10 is a flowchart showing an example of a molecule detecting method of the second embodiment.

FIG. 12 is a flowchart showing an example of an operating method of the molecule detecting system of the third embodiment.

DETAILED DESCRIPTION

In general, according to one embodiment, a molecule detecting device comprises a capturing section, a releasing section, and a detecting section. The capturing section is configured to, by combining a target molecule and a solubilizing agent with each other and thereby creating a composite body, capture the target molecule in a carrier liquid. The releasing section is configured to make the composite body release the target molecule therefrom in the carrier liquid. The detecting section is configured to carry out detection of the target molecule in the carrier liquid.

Hereinafter, embodiments will be described with reference to the accompanying drawings. It should be noted that in each embodiment, substantially identical constituent members are denoted by identical reference symbols, and the descriptions of the members are partially omitted in some cases. The drawings are schematic views and a relationship between a thickness and planar dimension of each part, ratio between thicknesses of parts, and the like are different from those of the actual parts in some cases.

A molecule detecting device according to an embodiment is a device configured to capture target molecules in a carrier liquid and detect the target molecules inside the liquid. The molecule detecting device includes three units including a capturing section, releasing section, and detecting section. The capturing section is a unit containing therein a carrier liquid including a solubilizing agent and configured to capture the target molecules in the carrier liquid by combining the target molecules with the solubilizing agent and creating a composite body. The releasing section is a unit configured to release the target molecules from the composite body. The detecting section is a unit configured to carry out detection of the target molecules.

First Embodiment

Molecule Detecting Device

Figure 1:
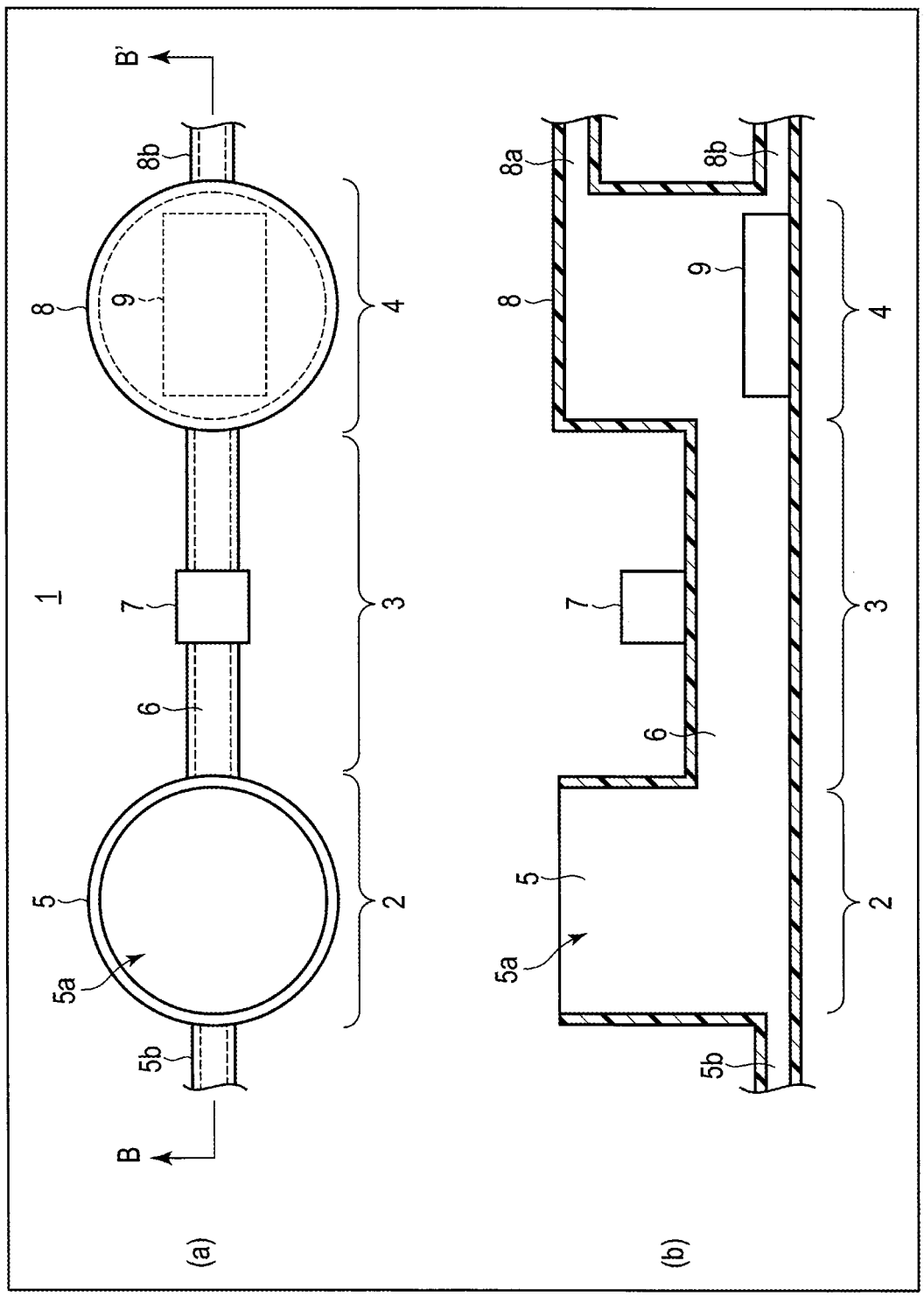
FIG. 1 shows a plan view and cross-sectional view each showing an example of a molecule detecting device of a first embodiment.

FIG. 1 is a view showing an example of a molecule detecting device 1 according to a first embodiment. (a) of FIG. 1 is a plan view of the molecule detecting device 1, and (b) of FIG. 1 is a cross-sectional view obtained by cutting the molecule detecting device 1 along line B-B'. The molecule detecting device 1 is provided with a first container 5, second container 8, and flow path 6 connecting the first container 5 and second container 8 to each other. In this description, "connection" implies connecting between a plurality of members with a pipe such as a flow path in such a manner that a liquid can move backward and forward between the plurality of members through the flow path.

The first container 5 functions as the capturing section 2. The first container 5 is a bottomed cylindrical container configured to accommodate therein, for example, a carrier liquid. For example, the first container 5 has an opening 5a configured to introduce the target molecules into the first container 5. Further, the first container 5 may also be provided with an incurrent pipe 5b configured to introduce the carrier liquid into the first container 5 in the vicinity of, for example, the bottom part thereof. The incurrent pipe 5b may also be connected to, for example, a tank configured to store therein, for example, the carrier liquid.

The flow path 6 functions as the releasing section 3. It is desirable that the flow path 6 should have a long and thin tubular shape and the inner diameter thereof be of the order of μm to mm.

A releasing means 7 is arranged in the middle of the longitudinal axis of the flow path 6. It is desirable that the releasing means 7 be, for example, a light irradiating device, temperature control device or pH adjusting device.

An example in which the releasing means 7 is a light irradiating device will be described below by using (a) of FIG. 2. The light irradiating device 20 can be provided, for example, on the outside of the flow path 6 or can be provided in such a manner as to be embedded in the material constituting the flow path 6. The light irradiating device 20 is provided with a light source 21, the light source 21 is opposed to the flow path 6, and can irradiate the inside of the flow path 6 with light. The light source 21 is, for example, a LED, semiconductor laser or the like. The type of the light source 21 and wavelength of light can be determined according to the types of the target molecules and/or solubilizing agent. In this case, it is desirable that the flow path 6 be formed of an optically transparent material.

An example in which the releasing means 7 is a temperature control device will be described below by using (b) of FIG. 2. The temperature control device 30 can be provided in such a manner as to cover, for example, the external surface of the flow path 6 or can be provided in such a manner as to be embedded in the material constituting the flow path 6. The temperature control device 30 can heat or cool the inside of the flow path 6. The temperature control device 30 is a device such as a heater or the like configured to carry out heating, and is provided with, for example, a heating wire 31. The heating wire 31 includes, for example, a coil, resistor or the like. Alternatively, the temperature control device 30 may be a device such as a Peltier element or the like configured to carry out cooling or may also be configured to carry out both heating and cooling.

An example in which the releasing means 7 is a pH adjusting device will be described below by using (c) of FIG. 2. The pH adjusting device 40 is provided with, for example, a third container 42 connected to the flow path 6 by a pipe 41. The pipe 41 is provided with, for example, a valve 43. Inside the third container 42, a pH adjuster 44 is accommodated. Although the pH adjuster 44 can be, for example, phosphoric acid, citric acid, succinic acid, tartaric acid, and the like, the pH adjuster 44 is not limited to these and may be a medicinal solution or buffer solution having a pH different from the liquid 12, high concentration salt or other chemical substances. The type and amount used of the pH adjuster 44 are selected according to the types of the target molecule 14, solubilizing agent 13 and/or carrier liquid 12.

Although details will be described later, the light irradiating device 20, temperature control device 30, and pH adjusting device 40 respectively have functions of applying stimuli respectively of light, temperature variation, and pH change to a composite body of the solubilizing agent and target molecules existing in the flow path 6 to thereby cause the composite body to release the target molecules. The releasing means 7 is not limited to the light irradiating device 20, temperature control device 30 or pH adjusting device 40, and may be other configurations as long as the configurations are to apply such a stimulus as to cause the composite body to release the target molecules.

In the flow path 6, a pump (not shown) configured to create a flow of the liquid from the first container 5 to the second container 8 may also be provided in between the containers 5 and 8.

As shown in FIG. 1, the second container 8 is provided with a sensor element 9. The second container 8 and sensor element 9 function as the detecting section 4.

The second container 8 is a cylindrical container in which the bottom and top are closed. The second container 8 may be provided with a drain pipe 8a configured to drain the liquid in the second container 8, in the vicinity of, for example, the bottom face thereof. Further, the second container 8 may be provided with an exhaust pipe 8b configured to discharge the gas in the second container 8 in the vicinity of, for example, the top face thereof. The drain pipe 8a and/or exhaust pipe 8b are connected to, for example, the tank storing therein the waste.

The sensor element 9 may have any configuration as long as the sensor element 9 is a sensor capable of detecting the target molecules. It is sufficient if the sensor element 9 is a sensor capable of detecting, for example, an electrical response, chemical reaction, optical response or weight variation attributable to the target molecules.

Figure 3:
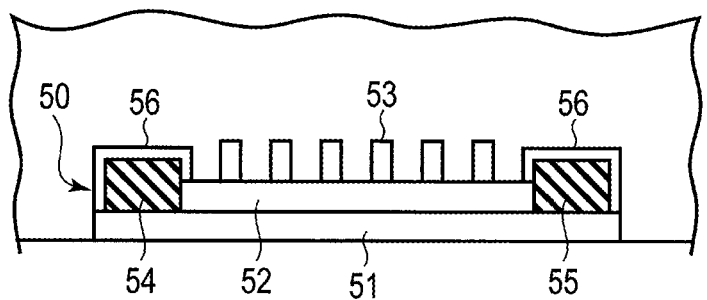
FIG. 3 is an enlarged cross-sectional view showing an example of a sensor element of the first embodiment.

It is desirable that the sensor element 9 be that using a field effect transistor (FET). A configuration example of such a sensor element will be described below by using FIG. 3. A sensor element 50 includes, for example, a sensitive membrane 52 formed on a substrate 51, and capturing body 53 fixed on the sensitive membrane 52 and configured to specifically combine with the target molecule. For example, a first electrode 54 is connected to one end of the sensitive membrane 52, and second electrode 55 is connected to the other end thereof. By applying a voltage to the first electrode 54 and second electrode 55 and measuring the value of the electric current between the first electrode 54 and second electrode 55, it is possible to detect a variation in the physical amount of the sensitive membrane 52 caused by the combining of the target molecule with the capturing body 53. Thereby, it is possible to detect the existence of the target molecules. The first electrode 54 and second electrode 55 are each coated with a protective film 56 in order that the electrodes 54 and 55 may not be brought into contact with the liquid accommodated in the second container 8.

The material for the substrate 51 is silicon, glass, ceramic, polymeric material or the like.

The sensitive membrane 52 is constituted of an electric conductor such as macromolecules, gold (Au), silver (Ag), copper (Cu), nickel (Ni), silicon (Si), silicide or the like or material, e.g., a two-dimensional material or the like such as graphene, carbon nanotube, molybdenum disulfide ($MoS_2$), tungsten diselenide ($WSe_2$) or the like. The sensitive membrane 52 has a shape of, for example, a singlefold or multiple film or nanowire.

The capturing body 53 is, for example, protein, peptide segments, antibody, aptamer, nucleic acid or the like. The type of the capturing body 53 is selected according to the type of the target molecules 14. It is desirable that as the capturing body 53, protein, peptide segments, antibody, aptamer, nucleic acid or the like specifically combining with the target molecules be used. The capturing body 53 may be an olfactory receptor or segment thereof. The segment can be a segment including a target-molecule specific binding site.

The material for the first electrode 54 and second electrode 55 is a metal such as gold (Au), silver (Ag), copper (Cu), palladium (Pd), platinum (Pt), nickel (Ni), titanium (Ti), chrome (Cr), aluminum (Al) or the like or conducting substance such as zinc oxide (ZnO), indium tin oxide (ITO), IGZO, conductive polymer or the like.

The protective film 56 is, for example, an insulating material. The insulating material is ceramic such as an oxide film, nitride film or the like and an insulating polymer or the like such as a polyimide or the like.

Although it is desirable that the sensor element 9 should have a measuring mechanism, the sensor element 9 may also have a configuration of a surface plasmon resonance (SPR)

element, surface acoustic wave (SAW) element, quartz crystal microbalance (QCM) element, microcantilever (MCL) element or the like. It is desirable that the sensitive membrane 52 to which the aforementioned capturing body 53 is fixed be provided on the surface of each of these elements so as to be used.

It is desirable that the first container 5, flow path 6, and second container 8 be formed of a material such as Si, $SiO_2$, SiN, ceramic glass, polyimide, polymeric material or the like. In the further embodiment, the first container 5 may have a shape of a flow path. In the further embodiment, one container or one flow path may be configured to be provided with both a capturing section 2 and releasing section 3.

Molecule Detecting Method

Next, a molecule detecting method using the molecule detecting device of the embodiment will be described below.

The molecule detecting method is a method for detecting target molecules in a sample. The sample is, for example, a gaseous body or liquid body expected to contain therein target molecules. The sample of the gaseous body is, for example, atmospheric air, exhalation, exhaust gas, gaseous body generated from a substance which is an object to be analyzed, atmospheric air around the substance which is the object to be analyzed or the like. As the substance which is the object to be analyzed, for example, a medicine, agricultural chemicals, food and drink, plants and animals, aromatic goods such as perfume or the like, freight or baggage, household articles or electric appliances, and the like are named.

The target molecule is, for example, a volatile organic compound (VOC) and is, for example, an odorous substance, pheromone substance or the like. Although the target molecule may be, for example, alcohol, ester, aldehyde or the like, the target molecule is not limited to these. The target molecule may be a chemical substance contained in, for example, a drug/stimulant, gunpowder, agricultural chemicals, perishable food, specific plants and animals or the like. The target molecule is, for example, a hydrophobic substance.

The sample of a liquid is, for example, a suspension of the abovementioned target molecules, or solution or the like obtained by dissolving the abovementioned target molecules in a buffer solution, water, organic solvent, mixture of a buffer solution and organic solvent, mixture or the like of water and organic solvent.

Figure 4:
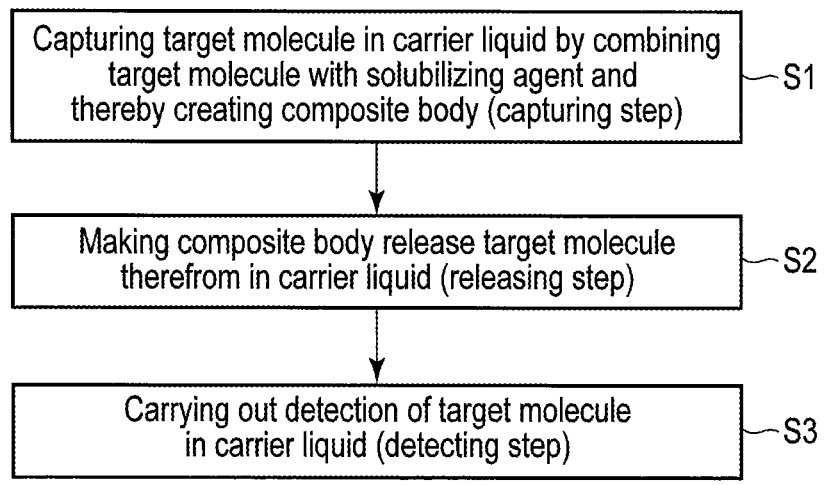
FIG. 4 is a flowchart showing an example of a molecule detecting method of the first embodiment.

The molecule detecting method includes the following steps as shown in FIG. 4.

(S1) capturing a target molecule in a carrier liquid by combining the target molecule with a solubilizing agent and thereby creating a composite body (capturing step), (S2) making the composite body release the target molecule therefrom in the carrier liquid (releasing step), and (S3) carrying out detection of the target molecule in the carrier liquid (detecting step).

Hereinafter, each of the steps of the molecule detecting method will be described in detail.

Figure 5:
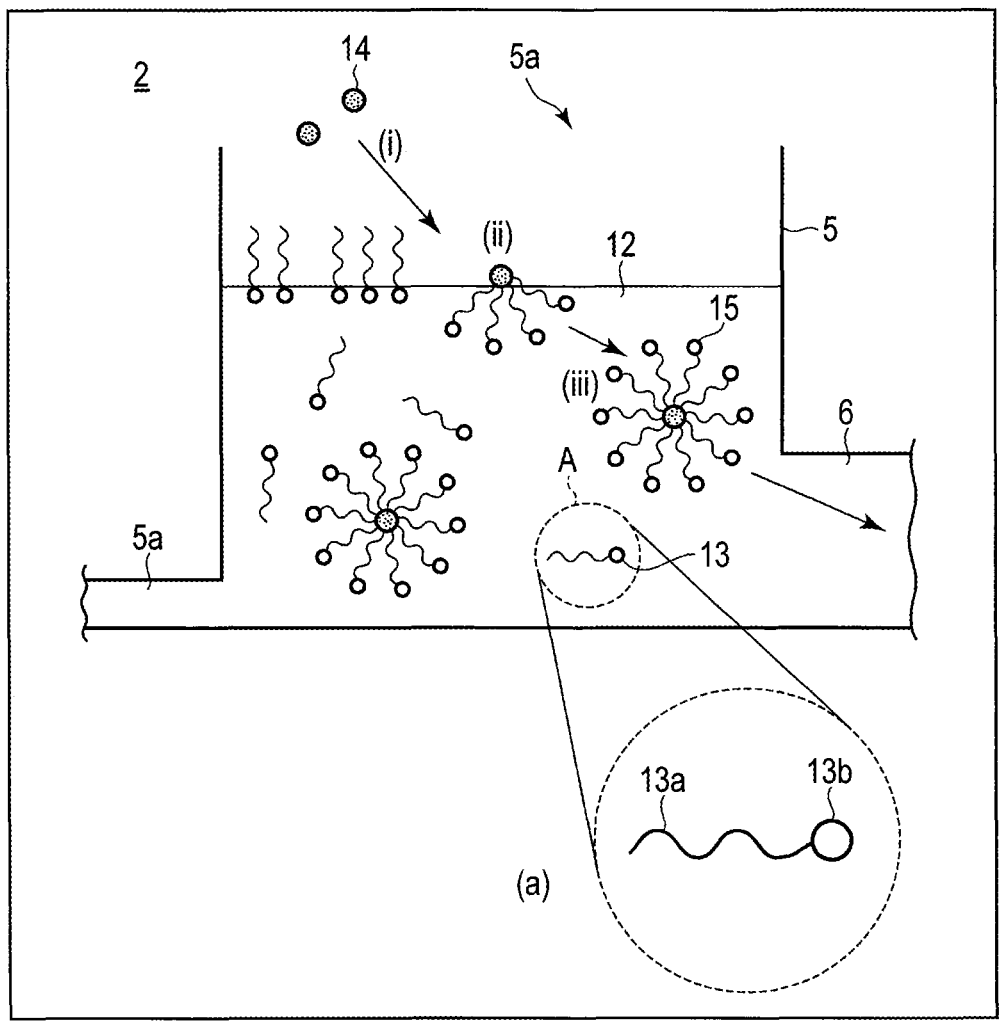
FIG. 5 is an enlarged view showing an example of a situation of a capturing section of the first embodiment in the usage state.

First, the molecule detecting device 1 and sample are prepared. Next, the capturing step S1 is carried out. The capturing step will be described below by using FIG. 5. The carrier liquid 12 is accommodated in the first container 5 serving as the capturing section 2. The carrier liquid 12 is introduced from, for example, the incurrent pipe 5b. At this time, the carrier liquid 12 may be made to flow into the flow path 6 and second container 8.

The carrier liquid 12 is, for example, water, physiological liquid, ionic liquid, PB buffer, PBS buffer, DMF, DMSO, organic solvent such as alcohol or the like or mixture of some of these liquids. The carrier liquid is not limited to the above, and may be other buffers.

The carrier liquid 12 contains therein the solubilizing agent 13. The solubilizing agent 13 may be mixed in advance into the carrier liquid 12 or may be added to the first container 5 later. Although the material for the solubilizing agent 13 will be described later, the material is constituted of, for example, amphipathic molecules each of which has both a hydrophobic section 13a and hydrophilic section 13b.

The carrier liquid 12 contains therein the solubilizing agent 13, whereby it is possible to capture the target molecules 14 in the carrier liquid 12 in, for example, the following manner. First, the sample is introduced into the first container 5 from the opening 5a (FIG. 5, portion (i)). When the target molecules 14 are contained in the sample, the target molecule 14 combines with the hydrophobic sections 13a of the solubilizing agent 13 at, for example, the surface of the carrier liquid 12 (FIG. 5, portion (ii)). As a result, a micelle-like composite body 15 configured by surrounding one target molecule 14 by a plurality of molecules of the solubilizing agent 13 is created, whereby the target molecule 14 is captured in the carrier liquid 12 (FIG. 5, portion (iii)). In the further embodiment, a composite body 15 in which a plurality of target molecules 14 combine with one molecule of the solubilizing agent 13 can be obtained in some cases. After the capturing step S1, the carrier liquid 12 may be stirred and/or left as it is until the target molecules 14 are sufficiently captured therein.

Figure 6:
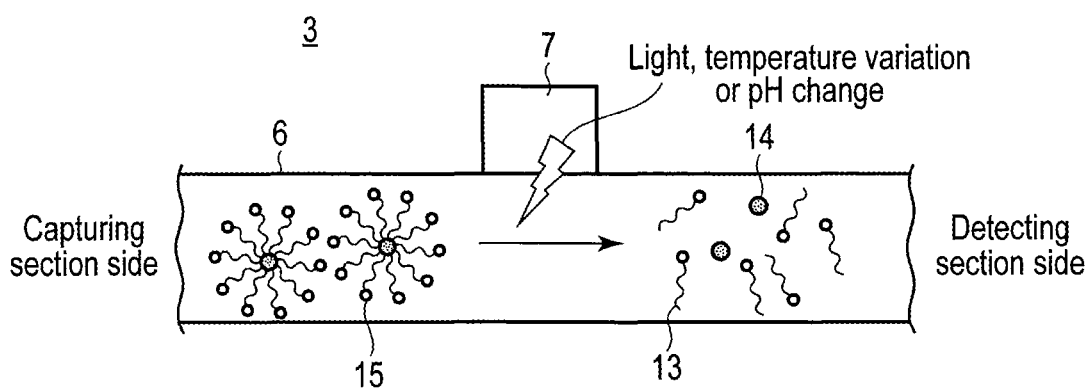
FIG. 6 is an enlarged view showing an example of a situation of the releasing section of the first embodiment in the usage state.

Subsequently, the obtained composite bodies 15 are made to flow into the flow path 6 and then the releasing step S2 is carried out. The releasing step S2 will be described below by using FIG. 6 which is an enlarged view of the releasing section 3. The composite body 15 receives a stimulus of light, temperature variation, pH change or the like from the releasing means 7 on the way of flowing inside the flow path 6 toward the second container 8 side, whereby the composite body 15 releases the target molecule 14 therefrom.

For example, when the light irradiating device 20 is used, by turning on the switch of the light irradiating device 20, the composite bodies 15 existing in the flow path 6 are irradiated with light 22 from the light source 21. Although the wavelength, irradiation time, intensity, and the like of the light 22 are appropriately adjusted according to the types of the target molecule 14 and solubilizing agent 13, it is desirable that light irradiation be continued until the target molecules 14 are released in sufficient amounts. Further, it is also desirable that light irradiation be continued until the target molecules 14 flow to (reach) the detecting section 4.

When the temperature control device 30 is used, by turning on the switch of the temperature control device 30, the temperature around the composite bodies 15 existing in the flow path 6 is varied. The temperature variation may be that of either heating or cooling. Although the amount of variation in temperature, heating or cooling time and the like are appropriately adjusted according to the types of the target molecules 14 and solubilizing agent 13, it is desirable that the temperature after the variation be maintained until the target molecules 14 are released in sufficient amounts. Further, it is also desirable that the maintenance of the temperature be carried out until the target molecules 14 flow to (reach) the detecting section 4.

When the pH adjusting device 40 is used, it is sufficient if the valve 43 of the pH adjusting device 40 is opened, and pH adjuster 44 is poured into the flow path 6. For example, pouring can be carried out by crushing the third container 42 or pumping air into the third container 42. Thereby, the pH around the composite bodies 15 existing in the flow path 6 is changed. The type, poured amount, amount of change in pH, and the like of the pH adjuster 44 are appropriately adjusted according to the types of the target molecule 14 and solubilizing agent 13. Thereafter, the inside state of the flow path 6 may be left as it is until the target molecules 14 are released in sufficient amounts.

Figure 7:
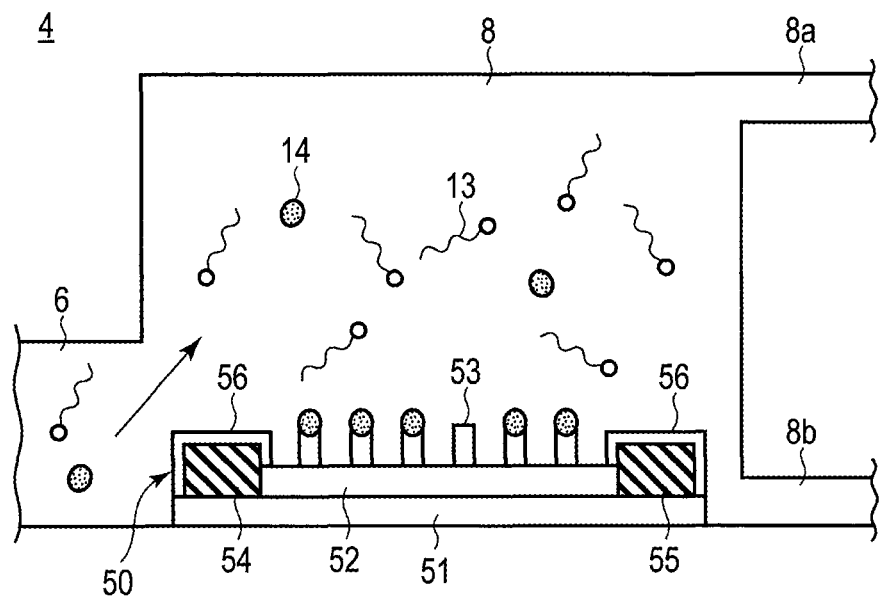
FIG. 7 is an enlarged view showing an example of a situation of the detecting section of the first embodiment in the usage state.

Next, the released target molecules 14 are made to flow into the second container 8. The target molecules 14 are detected by the sensor element 9 in the second container 8 (detecting step S3). As shown in FIG. 7, when the FET sensor element 50 is used, the carrier liquid 12 containing therein the target molecules 14 is arranged on the sensitive membrane 52, and target molecules 14 combine with the capturing body 53. Thereby, the physical amount of the sensitive membrane 52 changes. For example, a voltage is applied between the first electrode 54 and second electrode 55 from the time before the target molecules 14 reach the second container 8, and the value of the current between both the electrodes is detected with time, whereby it is possible to detect changes in the physical mount of the sensitive membrane 52 as changes in the current value.

For example, when the sensitive membrane 52 changes in the physical amount or when the amount of a change exceeds a threshold, it is possible to determine that target molecules 14 exist in the sample. Alternatively, by measuring the amount of change in advance with respect to the target molecules 14 of a known concentration, and preparing a calibration curve in advance, it is also possible to calculate the concentration of the target molecules 14 from the amount of change.

On the other hand, the solubilizing agent 13 and other non-detection object molecules hardly combine with the capturing body 53, and hence it is possible to detect the target molecules 14 with a high degree of sensitivity.

After completing the detection, the carrier liquid 12 is thrown away from, for example, the drain pipe 8a. When a gaseous body is produced inside the second container 8, the gaseous body may be discharged from the exhaust pipe 8b of the second container 8.

According to the molecule detecting device and molecule detecting method described above, by combining the target molecules 14 with the solubilizing agent 13 to thereby capture the target molecules 14 in the carrier liquid 12, it is possible to capture a larger number of target molecules 14 in the liquid. Further, by thereafter carrying out release of the target molecules 14 by the releasing section 3, it is possible to return the target molecules 14 from the state of the composite body 15 where it is difficult to detect the target molecules by means of the sensor element 9 to the dissociated state where the target molecules 14 can be detected more easily. As a result, it is possible to transfer more target molecules 14 in the dissociated state to the detecting section, and detection of a high signal/noise (S/N) ratio is enabled. As a result, even when the number of the target molecules is small, high-sensitivity detection is enabled.

The solubilizing agent 13 is a substance configured to form a composite body 15 by, for example, reversibly combining with target molecules 14 thereby bringing the target molecules 14 into a state where the target molecules 14 can exist in the carrier liquid 12, and release the target molecules 14 by a stimulus of light, temperature variation, pH change or the like to be given by the releasing means 7. In this description, "combination" includes both of chemical combination and mutual interaction.

The solubilizing agent 13 is constituted of, for example, amphipathic molecules. Alternatively, the solubilizing agent 13 may not be amphipathic molecules if the solubilizing agent 13 is a substance making it possible to capture the target molecules 14 in a liquid.

When the light irradiating device 20 is used as the releasing means 7, it is desirable that a substance ready to release the target molecules 14 by the stimulus of light be used as the solubilizing agent 13. For example, as a substance configured to release the target molecules 14 by ultraviolet light or near-infrared light, dextran-graft-(2-diazo-1,2-naphthoquinone) copolymer (following chemical formula) can be used.

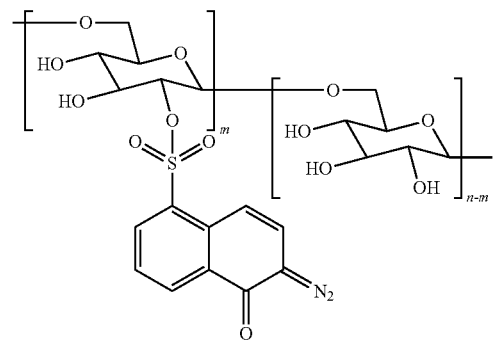

Dextran-graft-(2-diazo-1,2-naphthoquinone) Copolymer

When the temperature control device 30 is used as the releasing means 7, it is desirable that the solubilizing agent 13 be constituted of molecules releasing target molecules 14 by being changed in shape or the like by the temperature. For example, as such a solubilizing agent 13, poly (N-isopropylacrylamide) (following chemical formula) can be used.

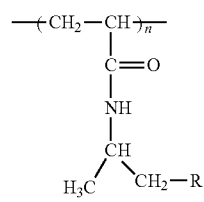

Poly (N-isopropylacrylamide)

In the above chemical formula, R is H, COOH, OH or $NH_2$.

When the pH adjusting device 40 is used as the releasing means 7, it is desirable that the solubilizing agent 13 be constituted of molecules releasing target molecules 14 by being changed in shape or the like by a pH change. For example, as such a solubilizing agent 13, odorant-binding protein (OBP) can be used. The OBP is contained in a mucous membrane of an olfactory organ, and has a function of transferring an odorous substance to an olfactory receptor. As an OBP, for example, an OBP2a (human), OBP1 (hog), OBP57 (fly), OBP3 (aphid), and the like are named. With respect to various types of odor molecules, corresponding OBPs are known and, when there is an OBP corresponding to the target molecule 14, the OBP may be used as the solubilizing agent 13. For example, when the target molecule 14 is limonene, it is desirable that the OBP3 be used as the solubilizing agent 13.

The solubilizing agent 13 is not limited to the above, and it is also possible to manufacture a desired solubilizing agent 13. For example, a material to be obtained by changing a substituent group of a material obtained from the past knowledge and configured to combine with a specific molecule or release the specific molecule therefrom on a specific condition of light, temperature or pH is prepared. The material is mixed with desired target molecules, and it is examined whether or not the target molecules are released from the material on a desired condition of light, temperature or pH by using a spectroscopic method such as dynamic light scattering, small-angle X-ray scattering, TEM, fluorescence spectroscopy, absorption spectroscopy or the like or by using a fluorescence microscope. Thereby, a desired solubilizing agent 13 is obtained.

Figure 8:
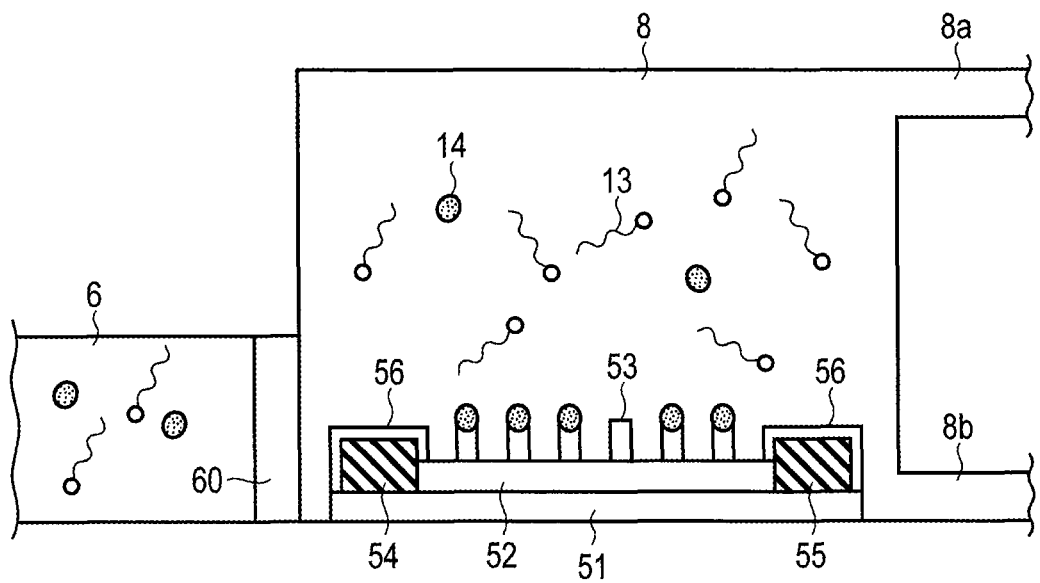
FIG. 8 is an enlarged view showing an example of a situation of the detecting section of the first embodiment in the usage state.

According to the further embodiment, as shown in FIG. 8, the molecule detecting device 1 may also be provided with a valve 60 placed between the releasing section 3 and detecting section 4. The valve 60 is provided at, for example, an end of the flow path 6 on the second container 8 side in such a manner as to block the flow path 6. The valve 60 is, for example, an electromagnetic valve. By closing the valve 60 in advance before starting to use the molecule detecting method, the carrier liquid 12 containing therein the solubilizing agent 13 is prevented from flowing into the detecting section 4, and non-detection object substance such as the solubilizing agent 13 or the like is prevented from nonspecifically combining with the sensor element 9. Further, by opening the valve 60 after the releasing step S2 is finished, and closing the valve 60 again to block the flow path 6 after the target molecules 14 have flowed into the second container 8, it is possible to prevent any further non-detection object substance from flowing into the second container 8.

According to the further embodiment, a further valve may be provided between the capturing section 2 and releasing section 3 (not shown). This valve is provided at, for example, an end of the flow path 6 on the first container 5 side in such a manner as to block the flow path 6. This valve is, for example, an electromagnetic valve. The valve may be closed in advance before starting to use the molecule detecting method, then the sample and carrier liquid 12 containing therein the solubilizing agent 13 may be introduced into the first container 5, and the composite body 15 may be made to flow into the flow path 6 by opening the valve after an elapse of time sufficient for the target molecules 14 to be captured in the carrier liquid 12.

Second Embodiment

According to a second embodiment, a molecule detecting device and molecule detecting method further provided with a separating section are provided. The separating section is provided between the releasing section 3 and detecting section 4, and separates the target molecules 14 and solubilizing agent 13 from each other.

As shown in FIG. 9, when the separating section 70 is provided, for example, the sensor element 9 is arranged close to the drain pipe 8a side in the second container 8, and the separating section 70 is provided at the vacated place on the flow path 6 side in the second container 8. The separating section 70 is provided with two electrodes placed in opposition to each other with a desired interval held between them, i.e., a third electrode 71 and fourth electrode 72.

The third electrode 71 is provided on, for example, the bottom surface of the second container 8. The fourth electrode 72 is provided on the ceiling surface of the second container 8 in such a manner as to be opposed to the third electrode 71. It is sufficient if the third electrode 71 and fourth electrode 72 are provided in such a manner that at least part of the third electrode 71 and fourth electrode 72 are exposed to the inside of the second container 8, and the third and fourth electrodes 71 and 72 may be provided in such a manner as to be respectively embedded in the bottom and ceiling of the second container 8. Further, a power source (not shown) configured to apply a voltage between the third electrode 71 and fourth electrode 72 is further provided.

Between the third electrode 71 and fourth electrode 72, an AC voltage may be applied or DC voltage may be applied. When an AC voltage is applied, it is desirable that one of the third electrode 71 and fourth electrode 72 be configured to be greater than the other.

Which one of the two electrodes 71 and 72 is to be made greater is selected according the types and combination of the solubilizing agent 13 and target molecules 14. When a DC voltage is applied, it is desirable that the sizes of the third electrode 71 and fourth electrode 72 be made identical to each other.

The molecule detecting method according to the second embodiment includes, as shown in FIG. 10, separating the solubilizing agent 13 (separating step) S4 between the releasing step S2 and detecting step S3.

When the separating section 70 shown in FIG. 9 is used, in the separating step S4, first, an electric field is formed between the third electrode 71 and fourth electrode 72 by applying a voltage between the third electrode 71 and fourth electrode 72. As a result, it is possible to attract the solubilizing agent 13 flowing from the flow path 6 to one of the electrodes, for example, the third electrode 71. Thereby, the solubilizing agent 13 is prevented from nonspecifically combining with the sensor element 9. As a result, it is possible to carry out detection with a high S/N ratio and stability.

Although the fourth electrode 72 may also be configured to attract the solubilizing agent 13, configuring the third electrode 71 closer to the flow path 6 to attract the solubilizing agent 13 makes it possible to collect more of the solubilizing agent 13 flowing from the flow path 6 than otherwise, and hence is more desirable than otherwise.

It is desirable that the position of the sensor element 9 be separated from the electrode to which the solubilizing agent 13 is to be attracted as distantly as possible, and it is desirable, for example, that both the above members be provided at positions diagonally opposite to each other. Thereby, it is possible to carry out detection with a high degree of accuracy. For example, in the case where the solubilizing agent 13 is attracted to the third electrode 71 as shown in FIG. 9, it is desirable that the sensor element 9 be arranged on the ceiling surface of the second container 8. However, both the members may also be provided on the same surface.

The third electrode 71 and fourth electrode 72 need not necessarily be provided respectively on the bottom surface and ceiling surface, and may also be provided on the sidewall or the like of the second container 8.

It is desirable that the valve 60 be provided as shown in FIG. 9, and after making the solubilizing agent 13 and target molecules 14 flow into the second container 8 subsequently to the releasing step S2, the valve 60 be closed and thereafter the separating step S4 and detecting step S3 be carried out. Thereby, the non-detection object substance such as the solubilizing agent 13 or the like does not enter the second container 8 during the separating step S4 and detecting step S3, and hence the solubilizing agent 13 is separated more efficiently. As a result, nonspecific adsorption is reduced and noise is also reduced, whereby detection with a high S/N ratio is enabled, and it is possible to detect the target molecules 14 with a higher degree of sensitivity. However, a configuration in which no valve 60 is provided is also acceptable.

Third Embodiment

Figure 11:
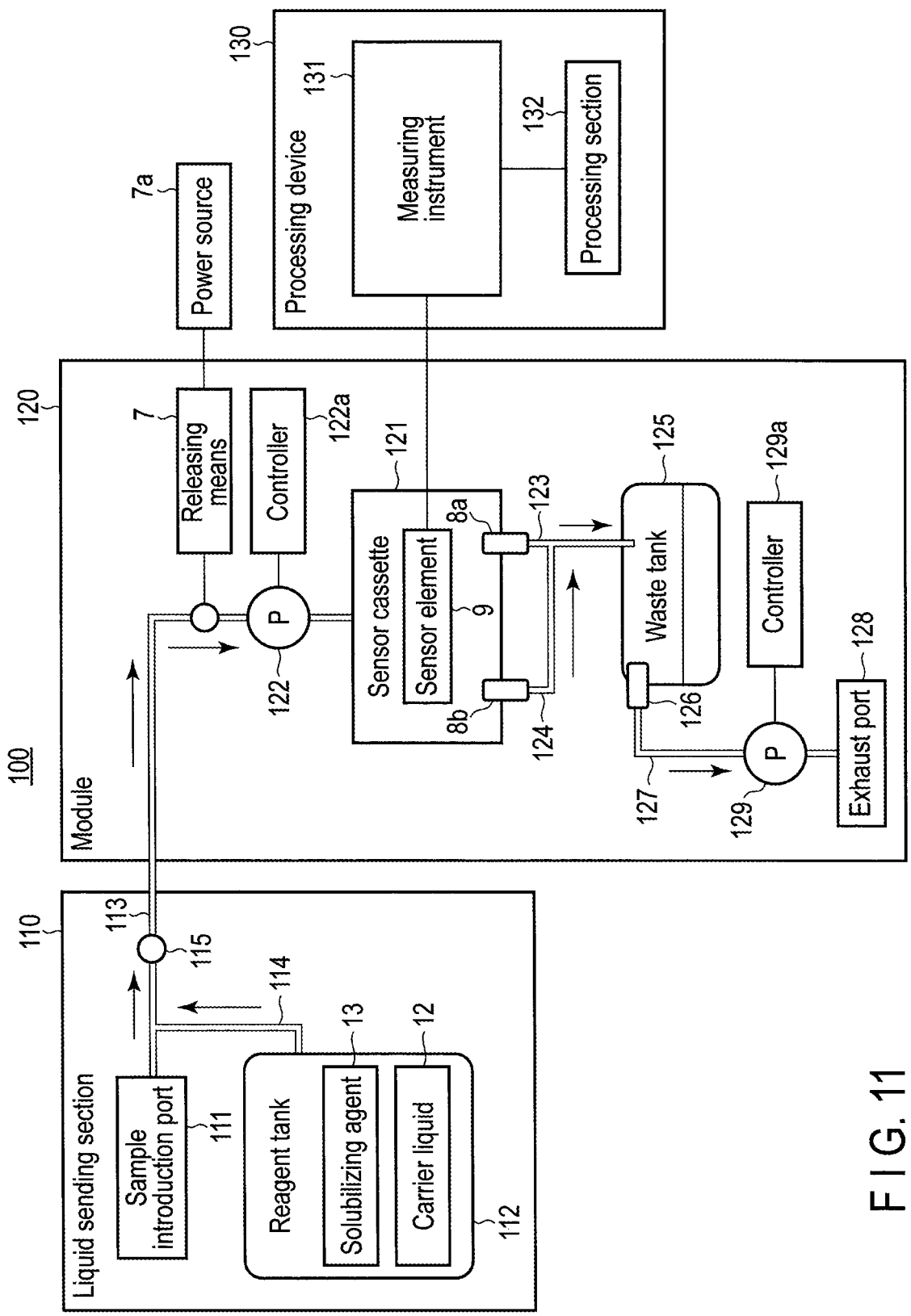
FIG. 11 is an enlarged view showing a molecule detecting system of a third embodiment.

In a third embodiment, a molecule detecting system is provided. As shown in FIG. 11, the molecule detecting system 100 is provided with a liquid sending section 110 functioning as the capturing section 2, module 120 functioning as both the releasing section 3 and detecting section 4 (and separating section 70 if necessary), and processing device 130 configured to carry out processing of an electric signal obtained by the detecting section 4 and control of each section included in the molecule detecting system 100.

The liquid sending section 110 is provided with a sample introducing port 111 for introducing the sample, and reagent tank 112. In the reagent tank 112, the carrier liquid 12 and solubilizing agent 13 dissolved in the carrier liquid 12 are stored.

The sample introducing port 111 is connected to a sensor cassette 121 of the module 120 through a first flow path 113. Further, the reagent tank 112 and first flow path 113 are connected to each other through a second flow path 114. On the sensor cassette 121 side of the confluence of the first flow path 113 and second flow path 114, a valve 115 is provided in between them.

Inside the module 120, the first flow path 113 is provided with a releasing means 7 and first pump 122 at positions on the upstream side of the sensor cassette 121.

The releasing means 7 is, for example, a light irradiating device 20, temperature control device 30, pH adjusting device 40 or the like described previously. The molecule detecting system 100 may further be provided with a controller (not shown) and power source 7a each configured to drive the releasing means 7.

The first pump 122 is, for example, a diaphragm pump or the like. To the first pump 122, a controller 122a configured to drive the first pump 122 may be connected.

The sensor cassette 121 is provided with a second container 8 (not shown) and sensor element 9 arranged inside the second container 8. For example, the end of the first flow path 113 is connected to the second container 8. The sensor cassette 121 may further be provided with a valve 60 and separating section 70 as the need arises.

The sensor cassette 121 is provided with a drain pipe 8a configured to drain the liquid from the second container 8 and exhaust pipe 8b configured to discharge the gas, and the drain pipe 8a is connected to a waste tank 125 configured to store therein the liquid and gas from the sensor cassette 121 through a third flow path 123. The exhaust pipe 8b is connected to the waste tank 125 through a fourth flow path 124 connected to the third flow path 123.

The waste tank 125 is provided with, for example, an exhaust pipe 126, and the exhaust pipe 126 is connected to an exhaust port 128 through a fifth flow path 127.

The fifth flow path 127 is provided with a second pump 129. The second pump 129 is, for example, a diaphragm pump or the like. To the second pump 129, a controller 129a configured to drive the second pump 129 may be connected.

The processing device 130 is provided with a measuring instrument 131 connected to the sensor element 9, and processing section 132 connected to the measuring instrument 131.

The measuring instrument 131 receives a signal obtained from the sensor element 9, measures the signal, and creates measurement value data. For example, the type of the measuring instrument 131 is selected according to the configuration of the sensor element 9. For example, when the sensor element 9 has the configuration of an FET, the signal is a current value between the first electrode 54 and second electrode 55, and the measuring instrument 131 can be provided with an ammeter configured to measure the current value. Further, when a QCM element is used as the sensor element 9, the signal is an oscillation frequency of the quartz substrate, and the measuring instrument 131 can be provided with a frequency measuring instrument. When an MCL element or SAW element is used as the sensor element 9, the signal is an oscillation frequency of the piezoelectric body, and the measuring instrument 131 is provided with a frequency measuring instrument.

The processing section 132 is provided with, for example, a memory, CPU, display section, input section, interface, and the like.

The processing section 132 may be a personal computer, smartphone, tablet terminal or the like. The processing section 132 is configured to carry out a mathematical operation of the measurement value data obtained from the measuring instrument 131. Further, for example, the processing section 132 may also be configured to be connected to the controller 122a and controller 129a of the pumps, and controller of each of the releasing means 7 through the interface, and transmit drive signals to these controllers.

The procedure for executing the molecule detecting method by using the molecule detecting system 100 will be described below. An example of the procedure is shown in FIG. 12.

Before carrying out detection, the carrier liquid 12 and solubilizing agent 13 are accommodated in advance in the reagent tank 112.

First, the valve 115 is opened in accordance with an instruction from the CPU in the processing section 132, first pump 122 is driven to make the sample flow from the sample introducing port 111 into the first flow path 113, and carrier liquid 12 containing therein the solubilizing agent 13 is made to flow from the reagent tank 112 into the second flow path 114 (S101). The carrier liquid 12 advances from the second flow path 114 to the first flow path 113, and comes into contact with the sample. Thereby, the target molecules in the sample combine with the solubilizing agent 13 and are captured in the carrier liquid 12. At this time, the valve 115 may be left closed until capturing of the target molecules sufficiently proceeds.

Next, in accordance with the instruction from the CPU, the first pump 122 is driven in the state where the valve 115 is opened, and carrier liquid 12 containing therein the composite bodies 15 is made to flow toward the vicinity of the releasing means 7. Subsequently, in accordance with the instruction of the CPU, the releasing means 7 is driven. As a result, when the composite bodies 15 flow to the position of the releasing means 7, the target molecules 14 are released from the composite bodies 15 (S102).

The released target molecules 14 flow toward the sensor cassette 121. Detection of the target molecules 14 is carried out by the sensor element 9 of the sensor cassette 121 (S103). The electric signal from the sensor element 9 is transmitted to the measuring instrument 131, measuring instrument 131 creates measurement value data from the electric signal, and measurement value data is stored in the memory of the processing section 132.

After the measurement is finished, the liquid body and gaseous body inside the sensor cassette 121 are thrown away into the waste tank 125 through the third flow path 123 and fourth flow path 124. The second pump 129 is driven in accordance with the instruction from the CPU, whereby the gaseous body inside the waste tank 125 is thrown away from the exhaust port 128 through the fifth flow path 127.

The CPU of the processing section 132 carries out a mathematical operation concerning presence/absence or the amount of the target molecules 14 from the measurement value data (S104). The operation result is displayed on, for example, the display section (S105).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A molecule detecting device comprising:
   a capturing section configured to, by combining a target molecule and a solubilizing agent with each other to thereby create a composite body, capture the target molecule in a carrier liquid;
   a releasing section configured to make the composite body release the target molecule therefrom in the carrier liquid; and
   a detecting section configured to carry out detection of the released target molecule in the carrier liquid,
   wherein:
      the releasing section includes a flow path connected, at its one end, to the capturing section, wherein the carrier liquid is introduced into the flow path from the capturing section, and the releasing section includes a light irradiating device irradiating an inside of the flow path with light, a temperature control device heating an inside of the flow path, or a pH adjusting device introducing a pH adjuster into the flow path,
      the detecting section includes a sensor element including a sensitive membrane including a capturing body which specifically combines with the released target molecule, and is configured to detect a variation in the physical amount of the sensitive membrane,
      the solubilizing agent includes amphipathic molecules each of which possesses a hydrophilic section and a hydrophobic section,
      the capturing section includes a first container in which the carrier liquid containing the solubilizing agent is accommodated and into which the target molecule is introduced so as to be contacted with the carrier liquid,
      the molecule detecting device further includes a second container to which another end of the flow path is connected and into which the carrier liquid is introduced, and
      the detecting section is accommodated in the second container.

2. The device of claim 1, wherein the target molecule is a hydrophobic molecule.

3. The device of claim 1, wherein the solubilizing agent is odorant-binding protein (OBP).

4. The device of claim 1, further comprising:
   a measuring instrument connected to the detecting section and configured to measure a signal obtained from the detecting section to thereby create measurement value data; and
   a processing device connected to the measuring instrument and configured to determine presence/absence or an amount of the target molecules on the basis of the measurement value data obtained from the measuring instrument.

5. A molecule detecting device comprising:
   a capturing section configured to, by combining a target molecule and a solubilizing agent with each other to thereby create a composite body, capture the target molecule in a carrier liquid;
   a releasing section configured to make the composite body release the target molecule therefrom in the carrier liquid; and
   a detecting section configured to carry out detection of the released target molecule in the carrier liquid,
   wherein:
      the releasing section includes a flow path connected, at its one end, to the capturing section, wherein the carrier liquid is introduced into the flow path from the capturing section, and the releasing section includes a light irradiating device irradiating an inside of the flow path with light,
      the detecting section includes a sensor element including a sensitive membrane including a capturing body which specifically combines with the released target molecule, and is configured to detect a variation in the physical amount of the sensitive membrane,
      the solubilizing agent includes amphipathic molecules each of which possesses a hydrophilic section and a hydrophobic section,
      the capturing section includes a first container in which the carrier liquid containing the solubilizing agent is accommodated and into which the target molecule is introduced so as to be contacted with the carrier liquid,
      the molecule detecting device further includes a second container to which another end of the flow path is connected and into which the carrier liquid is introduced,
      the detecting section is accommodated in the second container, and
      the solubilizing agent comprises dextran-graft-(2-diazo-1,2-naphthoquinone).

6. A molecule detecting device comprising:
   a capturing section configured to, by combining a target molecule and a solubilizing agent with each other to thereby create a composite body, capture the target molecule in a carrier liquid;
   a releasing section configured to make the composite body release the target molecule therefrom in the carrier liquid; and
   a detecting section configured to carry out detection of the released target molecule in the carrier liquid,
   wherein:
      the releasing section includes a flow path connected, at its one end, to the capturing section, wherein the carrier liquid is introduced into the flow path from the capturing section, and the releasing section includes a pH adjusting device introducing a pH adjuster into the flow path,
      the detecting section includes a sensor element including a sensitive membrane including a capturing body which specifically combines with the released target molecule, and is configured to detect a variation in the physical amount of the sensitive membrane, the solubilizing agent includes amphipathic molecules each of which possesses a hydrophilic section and a hydrophobic section, the capturing section includes a first container in which the carrier liquid containing the solubilizing agent is accommodated and into which the target molecule is introduced so as to be contacted with the carrier liquid, the molecule detecting device further includes a second container to which another end of the flow path is connected and into which the carrier liquid is introduced, the detecting section is accommodated in the second container, and the solubilizing agent comprises odorant-binding protein (OBP).

7. The device of claim 1, wherein the device further comprises:

a drain pipe which drains the carrier liquid from the second container, an exhaust pipe which discharges gas in the second container, and a separating section which is provided between the releasing section and the detecting section and includes two electrodes placed in opposition to each other with an interval between the two electrodes, the separating section separating the solubilizing agent from the target molecule, wherein the sensor element is arranged in the second container at a side of the drain pipe, and voltage is applied between the two electrodes.

* * * * *